United States Patent [19]

Majeti et al.

[11] Patent Number: 5,431,903
[45] Date of Patent: * Jul. 11, 1995

[54] ORAL COMPOSITIONS

[75] Inventors: Satyanarayana Majeti, Cincinnati; Michael F. Lukacovic, West Chester, both of Ohio

[73] Assignee: The Procter & Gamble Company, Cincinnati, Ohio

[*] Notice: The portion of the term of this patent subsequent to Jun. 14, 2011 has been disclaimed.

[21] Appl. No.: 206,302

[22] Filed: Mar. 3, 1994

Related U.S. Application Data

[63] Continuation of Ser. No. 998,710, Dec. 30, 1992, Pat. No. 5,320,831.

[51] Int. Cl.$^6$ .......................... A61K 7/16; A61K 7/18; A61K 7/24; A61K 7/28
[52] U.S. Cl. ......................... 424/52; 424/49; 424/50; 424/55
[58] Field of Search ....................... 424/49–58

[56] References Cited

U.S. PATENT DOCUMENTS

| | | | |
|---|---|---|---|
| 3,696,191 | 10/1972 | Weeks | 424/50 |
| 3,991,177 | 11/1976 | Vidra et al. | 424/50 |
| 4,011,309 | 3/1977 | Lutz | 424/49 |
| 4,058,595 | 11/1977 | Colodney | 424/50 |
| 4,115,546 | 9/1978 | Vidra et al. | 424/50 |
| 4,138,476 | 2/1979 | Simonson et al. | 424/50 |
| 4,138,477 | 2/1979 | Gaffar | 424/52 |
| 4,140,758 | 2/1979 | Vidra et al. | 424/50 |
| 4,154,815 | 5/1979 | Pader | 424/50 |
| 4,169,817 | 10/1979 | Weber | 252/545 |
| 4,183,914 | 1/1980 | Gaffar et al. | 424/48 |
| 4,518,694 | 5/1985 | Shaer | 435/180 |
| 4,652,444 | 3/1987 | Maurer | 424/49 |
| 4,708,864 | 11/1987 | Maurer | 424/49 |
| 4,725,428 | 2/1988 | Miyahara et al. | 424/50 |
| 4,737,359 | 4/1988 | Eigen et al. | 424/50 |
| 4,842,847 | 6/1989 | Amjad | 424/52 |
| 4,980,152 | 12/1990 | Frazier et al. | 424/52 |
| 4,986,981 | 1/1991 | Glace et al. | 424/50 |
| 4,992,420 | 2/1991 | Neeser | 514/8 |
| 5,000,939 | 3/1991 | Dring et al. | 424/48 |
| 5,041,236 | 8/1991 | Carpenter et al. | 252/174.12 |
| 5,089,163 | 2/1992 | Aronson et al. | 252/135 |
| 5,094,840 | 3/1992 | Isobe et al. | 424/50 |
| 5,145,665 | 9/1992 | Klueppel et al. | 424/50 |
| 5,213,790 | 5/1993 | Lukacovic et al. | 424/52 |

*Primary Examiner*—Shep K. Rose
*Attorney, Agent, or Firm*—David K. Dabbiere; Douglas C. Mohl; Jacobus C. Rasser

[57] ABSTRACT

Oral compositions, such as oral gels, toothpastes and mouthwashes, containing an enzyme, a surfactant, a chelating agent and a fluoride ion source.

16 Claims, No Drawings

ORAL COMPOSITIONS

This is a continuation of application Ser. No. 998,710, filed on Dec. 30, 1992, now U.S. Pat. No. 5,320,831.

TECHNICAL FIELD

The present invention relates to oral compositions containing an enzyme, a surfactant, a chelating agent and a fluoride ion source in a suitable oral carrier.

BACKGROUND OF THE INVENTION

The formation of dental plaque is the primary source of dental caries, gingival and periodontal disease and tooth loss. Dental plaque is a mixed matrix of bacteria, epithelial cells, leukocytes, macrophages and other oral exudate. Bacteria comprise approximately three-quarters of the plaque matrix. Any given sample of dental plaque could contain as many a 400 different varieties of microorganisms. This mix includes both aerobic and anaerobic bacteria, fungi and protozoa. Viruses have also been found in samples of dental plaque.

This matrix of organisms and oral exudate continues expanding and coalesces with other plaque growths situated nearby. The bacteria synthesize levans and glucans from sucrose found in the oral cavity providing energy for the microorganisms. These glucans, levans and microorganisms form an adhesive skeleton for the continued proliferation of plaque.

Calculus is a yellow or white mineralized deposit of bacterial plaque. Inorganic in nature, calculus consists primarily of calcium and magnesium phosphate and calcium carbonate. Calculus forms in layers as does plaque and is simply the mineralization of plaque's layered bacteria. Calculus is formed when plaque's protein-carbohydrate matrix accumulates calcium followed by the precipitation and mineralization of crystalline calcium phosphate. Once mineralized calculus is formed, another layer of bacteria adheres to the surface forming yet another layer of plaque which is subsequently mineralized into calculus.

The failure to retard or stop the proliferation of plaque is detrimental to oral health. Plaque formation leads to dental caries, gingival inflammation, periodontal disease and ultimately tooth loss. The present inventors recognize these problems and have developed a composition suitable for combating oral disease, preventing tooth loss, and leading to general oral well-being.

The use of a variety of agents to clean the oral cavity and reduce plaque and mouth malodor has been recognized for some time. Examples include: U.S. Pat. No. 3,696,191, Oct. 3, 1972 to Weeks; U.S. Pat. No. 3,991,177, Nov. 9, 1976 to Vidra et al.; U.S. Pat. No. 4,058,595, Nov. 15, 1977 to Colodney; U.S. Pat. No. 4,115,546, to Vidra et al.; U.S. Pat. No. 4,138,476, Feb. 6, 1979 to Simonson et al.; U.S. Pat. No. 4,140,758, Feb. 20, 1979 to Vidra et al.; U.S. Pat. No. 4,154,815, May 15, 1979 to Pader; U.S. Pat. No. 4,737,359, Apr. 12, 1988 to Eigen et al.; U.S. Pat. No. 4,986,981, Jan. 22, 1991 to Glace et al.; U.S. Pat. No. 4,992,420, Feb. 12, 1991 to Nesser; U.S. Pat. No. 5,000,939, Mar. 19, 1991 to Dring et al.; Kokai 02/105,898, published Apr. 18, 1990 to Kao Corporation; Kokai 03/128,313, published May 31, 1991 to Nippon Kotai Kenkyu and Kokai 03/223,209, published Oct. 2, 1991 to Lion Corporation; U.S. Pat. No. 4,652,444, Mar. 24, 1987 to Maurer; U.S. Pat. No. 4,725,428, Feb. 16, 1988 to Miyahara et al.; U.S. Pat. No. 4,355,022, Oct. 19, 1982 to Rabussay and PCT application WO 86/02831, published May 22, 1986 to Zetachron, Inc.

While the prior art discloses the use of various oral compositions for combating plaque, there is still a need for additional formulations which provide improved performance in combating oral disease along with increased user acceptance. The present inventors have discovered that by combining, in a suitable carrier, a chelating agent with a calcium binding coefficient of $10^2$ to $10^5$, a surfactant and an enzyme, superior cleaning results with an abatement in the formation of plaque and calculus.

It is therefore an object of the present invention to provide an oral care product and methods of using the same that are effective in arresting the accumulation of plaque and preventing gingivitis. It is a further object of the present invention to provide an oral product and methods that by reducing plaque will abate subsequent calculus formation. It is still a further object of the present invention to provide consumers with a product that will clean the oral cavity and provide improved methods of promoting vitality of the oral cavity.

These objectives and additional objectives will become readily apparent from the detailed description which follows.

SUMMARY OF THE INVENTION

The present invention relates to oral compositions which provide antiplaque, antigingivitis and anticalculus benefits with improved oral cleaning properties; comprising in one composition:

a) a safe and effective amount of a surfactant;
b) a safe and effective amount of an enzyme;
c) a safe and effective amount of a chelating agent having a calcium binding coefficient from about $10^2$ to about $10^5$;
d) a safe and effective amount of a fluoride ion source;
e) a suitable oral carrier; and wherein the composition is free of materials which complex with fluoride ions.

The present invention further relates to a method of reducing plaque, gingivitis and calculus using the above compositions.

All percentages and ratios herein are by weight unless otherwise specified. Additionally, all measurements are made at 25° C. unless otherwise specified.

DETAILED DESCRIPTION OF THE INVENTION

By "safe and effective amount," as used herein, means a sufficient amount to reduce plaque/gingivitis without harming the tissues and structures of the oral cavity.

By the term "suitable oral carrier," as used herein, means a suitable vehicle which can be used to apply the present compositions to the oral cavity in a safe and effective manner.

The compositions of this invention employ a safe and effective amount of a surfactant, an enzyme, a chelating agent having a calcium binding coefficient of about $10^2$ to about $10^5$, a fluoride ion source safe for use in the oral cavity and wherein the composition is free of materials which complex with fluoride ions contained in a suitable carrier. At the time of usage an amount of the composition is applied to the oral cavity. This amount of the composition is then preferably allowed to remain in contact with the tissues of the oral cavity for from about 15 seconds to about 12 hours. Alternatively, the composition could be left on indefinitely, or more practically until the composition is removed by a mechanical process; e.g., chewing foods or drinking liquids. This prolonged contact with the tissues of the oral cavity allows the composition to work for a period longer than conventional oral compositions that are applied and then brushed or rinsed away.

The pH of the present herein described compositions range from about 4.0 to about 9.0, with the preferred pH being from about 5.0 to about 7.0 and the most preferred pH being 5.0 to about 6.0.

The essential as well as optional components of the compositions of the present invention are described in the following paragraphs.

ESSENTIAL INGREDIENTS

Surfactants:

One of the essential agents required by the present invention is a surfactant or a mixture of compatible surfactants. Suitable surfactants are those which are reasonably stable throughout a wide pH range, i.e., non-soap anionic, cationic, nonionic or zwitterionic surfactants.

Suitable surfactants are described more fully in U.S. Pat. No. 3,959,458, May 25, 1976 to Agricola et al.; U.S. Pat. No. 3,937,807, Feb. 10, 1976 to Haefele; and U.S. Pat. No. 4,051,234, Sep. 27, 1988 to Gieske et al. These patents are incorporated herein by reference.

Preferred anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium auryl sulfate, sodium lauroyl sarcosinate and sodium coconut monoglyceride sulfonates are examples of anionic surfactants of this type. Mixtures of anionic surfactants can also be utilized.

Preferred cationic surfactants useful in the present invention can be broadly defined as derivatives of aliphatic quaternary ammonium compounds having one long alkyl chain containing from about 8 to 18 carbon atoms such as lauryl trimethyl ammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., herein incorporated by reference, where said quaternary ammonium fluorides have detergent properties. Certain cationic surfactants can also act as germicides in the compositions disclosed herein. Cationic surfactants such as chlorhexadine, although suitable for use in the current invention, are not preferred due to their capacity to stain the oral cavity's hard tissues. Persons skilled in the art are aware of this possibility and should incorporate cationic surfactants only with this limitation in mind.

Preferred nonionic surfactants that can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Preferred zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

The surfactant or mixtures of compatible surfactants can be present in the compositions of the present invention from about 0.1% to about 5.0%, preferably from about 0.3% to about 3.0% and most preferably from about 0.5% to about 2.0% by weight of the total composition. The surfactants best suited for inclusion into the present composition are: sodium alkyl sulfate, sodium lauroyl sarcosinate, cocoamidopropyl betaine and polysorbate 20, with sodium lauroyl sarcosinate being preferred and a combination of sodium lauroyl sarcosinate and cocoamidopropyl betaine being most preferred.

Chelating agents:

Chelating agents are able to complex calcium found in the cell walls of the bacteria. Binding of this calcium weakens the bacterial cell wall and augments bacterial lysis. However, it is possible to use a chelating agent which has an affinity for calcium that is too high. This results in tooth demineralization and is contrary to the objects and intentions of the present invention. The inventors have found a chelating agent with a calcium binding constant of about $10^2$ to $10^5$ provides improved cleaning with reduced plaque and calculus formation.

Another group of agents suitable for use as chelating agents in the present invention are the soluble pyrophosphates. The pyrophosphate salts used in the present compositions can be any of the alkali metal pyrophosphate salts. Specific salts include tetra alkali metal pyrophosphate, dialkali metal diacid pyrophosphate, trialkali metal monoacid pyrophosphate and mixtures thereof, wherein the alkali metals are preferably sodium or potassium. The salts are useful in both their hydrated and unhydrated forms. An effective amount of pyrophosphate salt useful in the present composition is generally enough to provide at least 1.0% pyrophosphate ion, preferably from about 1.5% to about 6%, more preferably from about 3.5% to about 6% of such ions. It is to be appreciated that the level of pyrophosphate ions is that capable of being provided to the composition (i.e., the theoretical amount at an appropriate pH) and that pyrophosphate forms other than $P_2O_7^{-4}$ (e.g., ($HP_2O_7^{-3}$)) may be present when a final product pH is established.

The pyrophosphate salts are described in more detail in Kirk & Othmer, *Encyclopedia of Chemical Technology*, Second Edition, Volume 15, Interscience Publishers (1968), incorporated herein by reference.

Still another possible group of chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and preferably S-97 Pharmaceutical Grade (M.W. 70,000), of GAF Chemicals Corporation.

Other operative polymeric polycarboxylates include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. both patents are incorporated herein by reference, and include copolymers of maleic anhydride with styrene, isobutylene or ethyl vinyl ether, polyacrylic, polyitaconic and polymaleic acids, and sulfoacrylic oligomers of M.W. as low as 1,000 available as Uniroyal ND-2.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

The linear anionic polymeric polycarboxylate component is mainly a hydrocarbon with optional halogen and oxygen containing substituents and linkages as present in for example ester, ether and OH groups, and when present is generally employed in the instant compositions in approximate weight amounts of about 0.05 to about 3%, preferably from about 0.05 to about 2%, more preferably from about 0.1 to about 2%.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight from 1,000–2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspattic acid, glutamic acid and phosphoserine, as disclosed in U.S. Pat. No. 4,866,161 Sep. 12, 1989 to Sikes et al., incorporated herein by reference.

All the above chelating agents are suitable for inclusion into the present invention, however, the polymeric polycarboxylates are preferred and a combination of citric acid and an alkali metal citrate salt is most preferred, with sodium citrate being the salt most preferred.

Enzymes:

Another of the essential components of the current invention is an enzyme or a mixture of several compatible enzymes. Enzymes are biological catalysts of chemical reactions in living systems. Enzymes combine with the substrates on which they act forming an intermediate enzyme-substrate complex. This complex is then converted to a reaction product and a liberated enzyme which continues its specific enzymatic function.

Enzymes provide several benefits when used for cleansing of the oral cavity. Proteases break down salivary proteins which are adsorbed onto the tooth surface and form the pellicle; the first layer of resulting plaque. Proteases along with lipases destroy bacteria by lysing proteins and lipids which form the structural component of bacterial cell walls and membranes. Dextranases break down the organic skeletal structure produced by bacteria that forms a matrix for bacterial adhesion. Proteases and amylases, not only prevent plaque formation, but also prevent the development of calculus by breaking-up the carbohydrate-protein complex that binds calcium, preventing mineralization.

Useful enzymes include any of the commercially available proteases, glucanohydrolases, endoglycosidases, amylases, mutanases, lipases and mucinases or compatible mixtures thereof. Preferred are the proteases, dextranases, endoglycosidases and mutanases, most preferred being papain, endoglycosidase or a mixture of dextranase and mutanase. Additional enzymes suitable for use in the present invention are disclosed in U.S. Pat. No. 5,000,939 to Dring et al., Mar. 19, 1991, U.S. Pat. No. 4,992,420 to Neeser, Feb. 12, 1991, U.S. Pat. No. 4,355,022 to Rabussay, Oct. 19, 1982, U.S. Pat. No. 4,154,815 to Pader, May 15, 1979, U.S. Pat. No. 4,058,595 to Colodney, Nov. 15, 1977, U.S. Pat. No. 3,991,177 to Virda et al., Nov. 9, 1976 and U.S. Pat. No. 3,696,191 to Weeks, Oct. 3, 1972 all incorporated herein by reference. An enzyme or a mixture of several compatible enzymes in the current invention constitutes from about 0.002% to about 2.0%, preferably from about 0.05% to about 1.5% and most preferably from about 0.1% to about 0.5%.

Fluoride ion source:

A fluoride ion source is an essential ingredient of the present invention. Fluoride ion sources are added to the present inventions at a level of from about 0.01% to 3.0%, preferably from about 0.03% to 1.0%, by weight of the composition. Fluoride ions combine with dental enamel and thereby reduce enamel solubility in acid. Application of fluoride ions to dental enamel serves to protect teeth against decay.

A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al., both being incorporated herein by reference. Representative fluoride ion sources include: Stannous fluoride, sodium fluoride, potassium fluoride, sodium monofluorophosphate and many others. Stannous fluoride and sodium fluoride are particularly preferred, as well as mixtures thereof.

OPTIONAL INGREDIENTS

In addition to the above described essential components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, Apr. 2, 1991 to Majeti; U.S. Pat. No. 4,885,155, Dec. 5, 1989 to Parran, Jr. et al.; U.S. Pat. No. 3,959,458, May 25, 1976 to Agricola et al. and U.S. Pat. No. 3,937,807, Feb. 10, 1976 to Haefele, all being incorporated herein by reference.

Abrasives:

Abrasive polishing materials might also be incorporated into dentifrice compositions of the present invention. Suitable abrasives can be any material which does not excessively abrade dentin and does not provide calcium ions that may precipitate with, for example, the fluoride ions provided by any included fluoride ion source or that might complex with the composition's chelating agent. Suitable abrasives include, for example, silicas including gels and precipitates, insoluble sodium polymetaphosphate, beta-phase calcium pyrophosphate and resinous abrasive materials such as particulate condensation product of urea and formaldehyde, and others such as compounds disclosed in U.S. Pat. No. 3,070,510, Dec. 25, 1962, to Cooley et al. incorporated herein by reference. Combinations of abrasives may also be used. Abrasives such as calcium carbonate, calcium phosphate and regular calcium pyrophosphate are not preferred for use in the present composition since they contain calcium ions that have the ability to complex with either an included fluoride ion source or the invention's chelating agent.

Silica dental abrasives, of various types, can contribute the characteristic benefits of superior dental cleaning and polishing without excessively abrading tooth enamel or dentin. Silica abrasives materials are also exceptionally compatible with the essential and optional components of the present invention. For these reasons silica abrasives are preferred for use within the present invention.

The silica abrasive polishing materials useful herein, as well as the other abrasives, generally have an average particle size ranging between about 0.1 and 30 microns, preferably from between 5 and 15 microns. The included silica abrasives can be from precipitated silica or silica gels, such as the silica xerogels described in U.S. Pat. No. 3,538,230, Mar. 2, 1970 to Pader et al. and U.S. Pat. No. 3,862,307, Jun. 21, 1975 to Digiulio, both incorporated herein by reference. Preferred silica xerogels are marketed under the trade name "Syloid" by the W. R. Grace & Co., Davison Chemical Division. The preferred precipitated silica materials include those marketed by the J. M. Huber Corp. under the trade name, "Zeodent"; especially the silica carrying the designation "Zeodent 119". These silica abrasives are described in U.S. Pat. No. 4,340,583, Jul. 29, 1982 to Wason, incorporated herein by reference.

The abrasives in the compositions described herein are incorporated at a level from about 6% to about 70%, preferably from about 15% to about 30% when the oral composition is a dentifrice toothpaste.

Flavoring agents:

Flavoring agents can also be added to oral dentifrice compositions of the present invention. Appropriate flavoring agents include oil of wintergreen, oil of peppermint, oil of spearmint, oil of sassafras, oil of clove and any other of the many known flavoring agents or combinations thereof.

Sweeting agents:

Possible sweeting agents which may be included for use in the present invention include: aspartame, acesulfame, saccharin, dextrose, levulose and sodium cyclamate. Flavoring and sweeting agents are customarily used in oral dentifrice compositions at levels from about 0.005% to about 2% by weight.

Water:

Water may also be present in the oral compositions of this invention. Water, employed in the preparation of commercial oral compositions should, preferably, be deionized and free of organic impurities. Water commonly comprises from about 10% to 50%, preferably from about 20% to about 40% and most preferably from about 10% to about 15% by weight of the oral compositions described herein. This amount of water includes the free water which is added plus that amount which is introduced with other materials such as with sorbitol or any components of the invention.

Thickening agents:

In preparing oral compositions, it is sometimes necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. Thickening agents in an amount from 0.5% to 5.0% by weight of the total composition can be used.

Another agent useful as an additional anticalculus agent is a metal ion source. Suitable metals include magnesium, zinc, copper, aluminum, iron and many others. These metals may be provided to the compositions as a water soluble salt (e.g. chloride) or chelated with a suitable chelating agent such as ethylene diamine tetracetic acid or phosphocitrate as well as others such as those disclosed in Kokai 61/36,211, Feb. 20, 1986 to Kito et al., incorporated herein by reference. Another reference disclosing suitable chelates is EPO Application 0265186, Apr. 27, 1988 to White, incorporated herein by reference.

Humectants:

Within oral compositions, it is also desirable to incorporate a humectant to prevent the composition from hardening upon exposure to air. Certain humectants can also impart desirable sweetness or flavor to dentifrice compositions. The humectant, on a pure humectant basis, generally comprises from about 15% to about 70%, preferably from about 30% to about 65%, by weight of the dentifrice composition.

Suitable humectants include edible polyhydric alcohols such as glycerine, sorbitol, xylitol, propylene glycol as well as other polyols and mixtures of these humectants. Mixtures of glycerine and sorbitol are especially preferred as the humectant component of the toothpaste compositions herein.

Adhesives:

In the compositions of the present invention, an adhesive is also desirable helping the active ingredients to adhere to the tissues of the oral cavity. Suitable adhesives include both polymers with limited water solubility as well as polymers lacking water solubility. These polymers deposit a thin film on both the oral cavityrs soft and hard tissues when saliva combines with the instant composition. Suitable limited water solubility adhesives include: hydroxy ethyl or propyl cellulose. Adhesives lacking water solubility include: ethyl cellulose, polyox resins and silicones. Adhesives lacking water solubility are incorporated into the instant invention by using a small amount of ethyl alcohol or another alcohol safe for use in the oral cavity and the human body.

Another possible adhesive suitable for use in the instant composition is polyvinylpyrrolidone ("PVP") with a molecular weight of about 50,000 to about 300,000, a suitable PVP is available from GAF Chemicals Corporation.

Still another possible adhesive suitable for use in the instant composition is a combination of Gantrez and the semisynthetic, water-soluble polymer carboxymethyl cellulose ("CMC"). Preferred is a mixture of 2:1 to 1:1 (Gantrez to CMC). Suitable for use in the combination is Gantrez with a M.W. of about 30,000 to about 1,000,000 available from GAF Chemicals Corporation and CMC with a M.W. of about 90,000 to about 700,000 available from Aqualon Company.

METHOD OF MANUFACTURE

The compositions of the present invention can be made using methods which are common in the oral product area.

COMPOSITION USE

The present invention in its method aspect involves applying to the oral cavity a safe and effective amount of the compositions described herein. These amounts (e.g. from about 0.3 to about 2 gm), if it is a toothpaste or toothgel is kept in the mouth from about 15 seconds to about 12 hours.

The following examples further describe and demonstrate preferred embodiments within the scope of the present invention. The examples are given solely for illustration and are not to be construed as limitations of this invention as many variations are possible without departing from the spirit and scope thereof.

EXAMPLE I

A dentifrice composition of the present invention contains the following components as described below.

| | |
|---|---|
| Sorbitol | 49.127 |
| Carbopol 956* | 0.250 |
| Xantham gum | 0.425 |
| Titanium dioxide | 0.525 |
| Silica | 20.000 |
| Citric acid | 0.900 |
| Sodium citrate | 5.000 |
| Sodium lauroyl sarcosinate (30% solution) | 4.000 |
| Endoglycosidase (3.2% solution) | 6.250 |
| Sodium fluoride | 0.243 |
| FD & C blue #1 | 0.050 |
| Flavor | 0.900 |
| Water | q.s. |
| Sodium Saccharin | 0.130 |

*Carboxyvinyl polymer supplied by B.F. Goodrich Company as Carbomer 956.

PROCEDURE FOR MAKING DENTIFRICE

Dentifrices of the instant composition are manufactured by setting the jacket temperature of a mixing tank to about 150° to about 165° degrees fahrenheit. The humectants and water are added to the mixing tank and agitation is started. When the temperature reaches approximately 120° add fluoride, sweetening agents, buffering agents, coloring agents and titanium dioxide. Premix thickening agents into the abrasive and add this mixture to the mixing tank with high agitation. Add surfactant to the combination and continue mixing. Cool tank to 120° add flavoring agents and continue mixing for approximately 5 minutes. Further cool the mixing tank to about 95° to about 100° and add the enzyme, mix for an additional 20 minutes.

Examples II–VIII are further examples of dentifrices of the present invention.

EXAMPLE II

| | |
|---|---|
| Sorbitol | 54.477 |
| Carbopol 956 | 0.250 |
| Xantham gum | 0.425 |
| Titanium dioxide | 0.525 |
| Silica | 20.000 |
| Citric acid | 0.900 |
| Sodium citrate | 5.000 |
| Sodium lauroyl sarcosinate (30% solution) | 2.667 |
| Cocoamidopropyl betaine (30% solution) | 2.667 |
| Papain | 0.500 |
| Sodium fluoride | 0.243 |
| FD & C blue #1 | 0.050 |
| Flavor | 0.900 |
| Water | q.s. |
| Sodium Saccharin | 0.130 |

EXAMPLE III

| | |
|---|---|
| Sorbitol | 25.672 |
| Glycerin | 20.000 |
| Carbopol 956 | 0.250 |
| Xantham gum | 0.425 |
| Titanium dioxide | 0.525 |
| Silica | 20.000 |
| Citric acid | 0.800 |
| Sodium citrate | 4.200 |
| Sodium lauroyl sarcosinate (30% solution) | 4.000 |
| Cocoamidopropyl betaine (30% solution) | 1.333 |
| Endoglycosidase (3.2% solution) | 9.375 |
| Sodium fluoride | 0.243 |
| FD & C blue #1 | 0.050 |
| Flavor | 1.000 |
| Water | q.s. |
| Sodium Saccharin | 0.130 |

EXAMPLE IV

| | |
|---|---|
| Sorbitol | 32.379 |
| Glycerin | 15.000 |
| Carboxymethyl cellulose | 0.800 |
| Titanium dioxide | 0.525 |

-continued

| | |
|---|---|
| Silica | 25.000 |
| Citric acid | 0.800 |
| Sodium citrate | 4.200 |
| Sodium alkyl sulfate (30% solution) | 2.000 |
| Sodium lauroyl sarcosinate (30% solution) | 2.000 |
| Cocoamidopropyl betaine (30% solution) | 0.333 |
| Papain | 0.400 |
| Sodium fluoride | 0.243 |
| FD & C blue #1 | 0.050 |
| Flavor | 1.000 |
| Water | q.s. |
| Sodium Saccharin | 0.270 |

EXAMPLE V

| | |
|---|---|
| Sorbitol | 36.757 |
| Glycerin | 10.000 |
| Carbopol 956 | 0.250 |
| Xantham gum | 0.425 |
| Titanium oxide | 0.525 |
| Silica | 30.000 |
| Citric acid | 0.600 |
| Sodium citrate | 3.000 |
| Sodium lauroyl sarcosinate (30% solution) | 3.333 |
| Cocoamidopropyl betaine (30% solution) | 1.667 |
| Papain | 0.500 |
| Sodium fluoride | 0.243 |
| FD & C blue #1 | 0.050 |
| Flavor | 0.900 |
| Water | q.s. |
| Sodium Saccharin | 0.250 |

EXAMPLE VI

| | |
|---|---|
| Sorbitol | 48.127 |
| Carbopol 956 | 0.250 |
| Xantham gum | 0.425 |
| Titanium oxide | 0.525 |
| Silica | 20.000 |
| Citric acid | 0.900 |
| Sodium citrate | 5.000 |
| Sodium lauroyl sarcosinate (30% solution) | 4.000 |
| Endoglycosidase (3.2% solution) | 6.250 |
| Sodium fluoride | 0.243 |
| FD & C blue #1 | 0.050 |
| Flavor | 0.900 |
| Water | q.s. |
| Sodium Saccharin | 0.130 |
| Mineral oil | 1.000 |

EXAMPLE VII

| | |
|---|---|
| Sorbitol | 54.377 |
| Carbopol 956 | 0.250 |
| Xantham gum | 0.425 |
| Titanium oxide | 0.525 |
| Silica | 20.000 |
| Citric acid | 1.500 |
| Sodium citrate | 4.500 |
| Sodium lauroyl sarcosinate (30% solution) | 2.667 |
| Cocoamidopropyl betaine (30% solution) | 2.667 |
| Papain | 0.500 |
| Sodium fluoride | 0.243 |
| FD & C blue #1 | 0.050 |

-continued

| | |
|---|---|
| Flavor | 0.900 |
| Water | q.s. |
| Sodium Saccharin | 0.130 |

EXAMPLE VIII

| | |
|---|---|
| Sorbitol | 61.814 |
| Carbopol 956 | 0.314 |
| Xantham gum | 0.534 |
| Citric acid | 1.132 |
| Sodium citrate | 6.291 |
| Sodium lauroyl sarcosinate (30% solution) | 5.033 |
| Endoglycosidase (3.2% solution) | 7.864 |
| Sodium fluoride | 0.305 |
| FD & C blue #1 | 0.062 |
| Flavor | 1.132 |
| Water | q.s. |
| Sodium Saccharin | 2.768 |

EXAMPLE IX

| | |
|---|---|
| Sorbitol | 68.546 |
| Carbopol 956 | 0.314 |
| Xantham gum | 0.534 |
| Citric acid | 1.132 |
| Sodium citrate | 6.291 |
| Sodium lauroyl sarcosinate (30% solution) | 3.355 |
| Cocoamidoprophyl betaine (30% solution) | 3.355 |
| Papain | 0.629 |
| Sodium fluoride | 0.305 |
| FD & C blue #1 | 0.062 |
| Flavor | 1.132 |
| Water | q.s. |
| Sodium Saccharin | 0.163 |

EXAMPLE X

| | |
|---|---|
| Sorbitol | 32.301 |
| Glycerin | 25.165 |
| Carbopol 956 | 0.314 |
| Xantham gum | 0.534 |
| Citric acid | 1.006 |
| Sodium citrate | 5.284 |
| Sldium lauroyl sarcosinate (30% solution) | 5.033 |
| Cocoamidopropyl betaine (30% solution) | 1.677 |
| Endoglycosidase (3.2% solution) | 11.179 |
| Sodium fluoride | 0.305 |
| FD & C blue #1 | 0.062 |
| Flavor | 1.258 |
| Water | q.s. |
| Sodium Saccharin | 0.163 |

EXAMPLE XI

| | |
|---|---|
| Sorbitol | 68.420 |
| Carbopol 956 | 0.314 |
| Xantham gum | 0.534 |
| Citric acid | 1.887 |
| Sodium citrate | 5.662 |
| Sodium lauroyl sarcosinate (30% solution) | 3.355 |
| Cocoamidopropyl betaine (30% solution) | 3.355 |

| | |
|---|---|
| -continued | |
| Papain | 0.629 |
| Sodium fluoride | 0.305 |
| FD & C blue #1 | 0.063 |
| Flavor | 1.132 |
| Water | q.s. |
| Sodium Saccharin | 0.163 |

In the above examples, substantially similar results are obtained when the surfactant(s), enzyme(s), chelating agent (s) and combinations thereof are substituted with other similar components herein disclosed and described.

What is claimed is:

1. An oral composition providing improved oral cleansing properties, comprising:
   a) a safe and effective amount of suffactant;
   b) a safe and effective amount of an enzyme;
   c) a safe and effective amount of a chelating agent selected from the group consisting of citric acid, alkali metal citrate, polymeric polycarboxylates, soluble pyrophosphates and mixtures thereof having a calcium binding coefficient of from about $10^2$ to about $10^5$;
   d) a safe and effective amount or a fluoride ion source;
   e) a suitable dentifrice or mouthwash oral carrier; and wherein the composition is free of materials which complex with fluoride ions and wherein said composition is free of the combination of citric acid and the alkyl metal citrate.

2. An oral composition according to claim 1 wherein the surfactant is selected from the group consisting of sodium lauroyl sarcosinate, sodium alkyl sulfate, cocoamidopropyl betaine, polysorbate 20 and mixtures thereof.

3. An oral composition according to claim 2 wherein the enzyme is selected from the group consisting of endoglycosidase, papain, dextranase, mutanase and mixtures thereof.

4. An oral composition according to claim 3 wherein the chelating agent is selected from the group consisting of citric acid, alkali metal citrate, polymeric polycarboxylates, soluble pyrophosphates and mixtures thereof.

5. An oral composition according to claim 4 wherein the fluoride ion source is selected from the group consisting of sodium fluoride, stannous fluoride, sodium monofluorophosphate, potassium fluoride and mixtures thereof.

6. An oral composition according to claim 5 which further comprises from about 15% to about 70% of a humectant selected from the group consisting of glycerin and sorbitol and mixtures thereof.

7. An oral composition according to claim 6 wherein the surfactant is present at a level from about 0.1% to about 5.0%

8. An oral composition according to claim 7 wherein the enzyme is present at a level from about 0.002% to about 2.0%.

9. An oral composition according to claim 8 which further comprises an abrasive.

10. A method of reducing and preventing plaque and gingivitis, comprising the application of a safe and effective amount of a composition according to claim 1, to the teeth and other oral surfaces.

11. A method of reducing and preventing plaque and gingivitis, comprising the application of a safe and effective amount of a composition according to claim 6, to the teeth and other oral surfaces.

12. A method of reducing and preventing plaque and gingivitis, comprising the application of a safe and effective amount of a composition according to claim 9, to the teeth and other oral surfaces.

13. A method of reducing and preventing plaque and gingivitis, comprising the application of a safe and effective amount of a composition according to claim 2 to the teeth and other oral surfaces.

14. A method of reducing and preventing plaque and gingivitis, comprising the application of a safe and effective amount of a composition according to claim 1 to the teeth and other oral surfaces wherein the composition is allowed to remain on the teeth and other oral surfaces for from about 15 seconds to about 12 hours.

15. A method of reducing and preventing plaque and gingivitis, comprising the application of a safe and effective amount of a composition according to claim 6 to the teeth and other oral surfaces wherein the composition is allowed to remain on the teeth and other oral surfaces for from about 15 seconds to about 12 hours.

16. A method of reducing and preventing plaque and gingivitis, comprising the application of a safe and effective amount of a composition according to claim 9 to the teeth and other oral surfaces wherein the composition is allowed to remain on the teeth and other oral surfaces for from about 15 seconds to about 12 hours.

* * * * *